United States Patent [19]
Jacobson et al.

[11] Patent Number: 5,513,645
[45] Date of Patent: May 7, 1996

[54] HOLTER FUNCTIONS WITH A ZOOM FEATURE

[75] Inventors: Peter Jacobson, Haguenau; Daniel Kroiss, Schweighouse-Moder, both of France

[73] Assignee: Ela Medical S.A., Montrouge, France

[21] Appl. No.: 340,240

[22] Filed: Nov. 16, 1994

[30] Foreign Application Priority Data

Nov. 17, 1993 [FR] France ................... 93 13734

[51] Int. Cl.⁶ .................................. A61B 5/0432
[52] U.S. Cl. ................ 128/710; 607/27; 128/705
[58] Field of Search ................... 128/710, 711, 128/702, 705, 696; 607/4, 14, 30, 27; 364/413.06

[56] References Cited

U.S. PATENT DOCUMENTS

| | | | |
|---|---|---|---|
| 4,295,474 | 10/1981 | Fischell | 128/697 |
| 4,374,382 | 2/1983 | Markowitz | 340/870.01 |
| 4,417,306 | 11/1983 | Citron et al. | 128/710 |
| 4,513,743 | 4/1985 | van Arragon et al. | 128/419 PG |
| 4,548,209 | 10/1985 | Wielders et al. | 128/419 D |
| 4,585,004 | 4/1986 | Brownlee | 607/27 |
| 5,052,399 | 10/1991 | Olive et al. | 128/703 |
| 5,088,488 | 2/1992 | Markowitz et al. | 607/27 |
| 5,306,293 | 4/1994 | Zacouto | 607/17 |

FOREIGN PATENT DOCUMENTS

| | | | |
|---|---|---|---|
| 0339471 | 4/1989 | European Pat. Off. | A61N 1/39 |
| 0487429 | 11/1991 | France | A61N 1/08 |

OTHER PUBLICATIONS

Chorus II, Implantable dual-chamber Pulse generator —DDD MO, Physician's Manual.

P. Attuel, J. Mugica, et al., Centre de Stimulation Cardiaque Val D'Or —Saint Cloud —France, Hopital Lariboisiere —Paris —France. CardioFrance —Noisy-le-Grand— France, Cardiac Pacing. Proceedings of the VIth World Symposium on Cardiac Pacing, Montreal, Oct. 2–5, 1979, Chapter 4–4.

Ripart, Jacobson, Technologie Des Memoires Et Fonction Holter Implantable, 1981, pp. 31–40.

*Primary Examiner*—William E. Kamm
*Assistant Examiner*—Kennedy J. Schaetzle
*Attorney, Agent, or Firm*—Orrick Herrington & Sutcliffe

[57] ABSTRACT

This invention provides an improved Holter function in an implantable device for arrhythmia monitoring or therapy. One improvement consists of a zoom feature which stores information about an arrhythmia episode at several levels of detail, with increasing levels of detail corresponding to shorter recording periods, and with a way to display the relation in time of the recordings at different levels of detail. The invention also introduces a novel implantable Holter function called an event log, which records time-stamped events once each minute, on changes in detected rhythm, or on application of antiarrhythmia therapy. The invention also provides logic for arbitrating which arrhythmia episodes the device saves in its memory.

34 Claims, 2 Drawing Sheets

FIG. 2

| HOLTER RECORDS | RECORD DESCRIPTION | | | |
|---|---|---|---|---|
| RECORD NO. 3 | TYPE EVENT | VF | RETRIEVE AND DISPLAY THE RECORD | ERASE THE RECORD |
| | YEAR | 93 | | |
| | MONTH | 09 | | |
| | DAY | 10 | | |
| | HOUR | 18 | | |
| | MINUTE | 32 | | |
| 19 | 20 | | 21 | 22 |

FIG. 3

| 18:52:04 | E1 | 18:52:16 | E2 | 18:53:22 | E3 | 18:54:22 | E4 |
|---|---|---|---|---|---|---|---|
| A:AVG (/MIN) | 125 | PROGR. STIMUL. | 1 | ARRHYTHMIA | TV | SHOCK PROGRAM | 2 |
| V:AVG (/MIN) | 85 | SEQUENCE | 10 | ACCELERATION | Ven | SEQUENCE | 3 |
| V:LAST (/MIN) | 100 | LAST VV (ms) | 125 | V:LAST (/MIN) | 188 | CHARGE TIME (s) | 12 |
| V:MAX (/MIN) | 154 | CYCLES PACED | 14 | % CORREL. PR | 22 | PRE-SHOCK ENERGY (J) | 34 |
| PVC (/MIN) | 3 | CYCLES SENSED | 1 | % CORREL. RR | 75 | DELIVERED ENERGY (J) | 26 |

23

HOLTER FUNCTIONS WITH A ZOOM FEATURE

FIELD OF THE INVENTION

This invention relates to an apparatus and method for processing and storing information about cardiac events in an implantable medical device, such as a device for cardiac monitoring and/or therapy, more particularly an implantable defibrillator.

BACKGROUND OF THE INVENTION

In general, functions which record events relating to cardiac activity have come to be known as Holter functions. Holter functions in an implantable device, which a user can interrogate at some later date via telemetry with an external programming and display device, have come to be known as implantable Holter functions. Telemetry refers to the wireless communications between the external programmer and the implanted medical device, which techniques are well known.

Cardiac signals measured with external electrodes are called electrocardiograms, whereas heart signals measured with implanted electrodes are called electrograms.

As used herein, a defibrillator refers to any device intended to revert a tachyarrhythmia with electrical energy substantially exceeding the energy provided by implantable cardiac pacemakers. This includes implantable defibrillator/cardioverter/pacemakers and implantable defibrillator / pacemakers. It should be understood that the present invention is applicable to such defibrillators as well as pacemakers which also perform a Holter function and devices that only perform a Holter function.

Holter functions for implantable medical devices have appeared in various forms in the prior art. U.S. Pat. No. 4,295,474 to Fischell, filed on Oct. 2, 1979, refers to an electrogram recording system, digitally storing in a first location the electrogram covering a period just prior to and including the occurrence of some physiological event, and in a second location storing the electrogram for a second period following the event. Fischell continuously stored the electrogram and "froze" it when the trigger event occurred, or at some predetermined time after the trigger event.

At the VIth World Symposium on Cardiac Pacing in Montreal, October 2 to 5, 1979, Attuel, Mugica, et al. presented an implantable pacemaker with a Holter function, which counted pauses in the heart rhythm. They proposed a future system which would identify bradycardia or tachycardia and record atrial and ventricular signals when detecting these arrhythmias.

In a publication entitled "Technologie des memoires et function Holter implantable", presented at Cardiostim in October 1980, Ripan and Jacobson discussed partitioning an available Holter memory in an implantable pacemaker. The pacemaker included a detector to classify arrhythmias. They proposed three schemes for storing information: (1) A two-second electrogram, triggered by a selected type of detected arrhythmia; (2) Sets of occurrence counters for selected types of arrhythmia, each set corresponding to a period of time in the history of the device; and (3) Histograms of cardiac intervals, each histogram also corresponding to a period of time.

U.S. Pat. No. 4,374,382 to Markowitz, filed in January 1981, refers to a system called marker channel telemetry. Markers consist of digital codes corresponding to cardiac events, such as atrial sensing, ventricular pacing, etc. The Markowitz device transmitted these codes via telemetry to an external receiver, as the corresponding events occurred. Markowitz did not durably store the marker codes in the implant for display when the user desires.

U.S. Pat. No. 4,513,743 to van Arragon, Mensink, et al., filed in November 1982, refers to an implantable pacemaker with cardiac interval histograms each corresponding to a period of time, similar to the concept first presented by Ripart and Jacobson in 1980 (supra).

U.S. Pat. No. 5,052,399 to Olive and Lincoln, filed in September 1990, refers to a method for encoding and compressing a record of consecutive cardiac cycle lengths, wherein the device stores the difference between lengths of successive cycles, or if this exceeds the capacity of a memory word, it stores the last cycle length.

ELA Medical, the assignee of this application, has since November 1991 sold a pacemaker under the tradename Chorus II, which includes an implantable Holter function called marker chains. The device stores a marker and then an item of information permitting one to determine the time when the marker occurred relative to the previous marked event. It stores a chain of such time-stamped markers, permitting an external programmer device to reconstruct a synthesized timing diagram of marked events, with the intervals between them.

SUMMARY OF THE INVENTION

It is thus apparent that manufacturers have made efforts toward automatic storage of arrhythmia information, in implantable cardiac therapy devices (mainly in pacemakers not having any cardioversion or alefibrillation function), for many years. Due to limited memory capacity, all such systems represent a compromise between the desire to store detailed information about individual heartbeats, and the desire to store information covering extended periods of time, or covering many arrhythmia episodes. In general, the higher the level of detail, the shorter the recording that fits in a given amount of memory.

Considering this dilemma by analogy to photography, users of cameras with zoom lenses understand the compromise here. When the user "zooms in" to obtain more detail, the size of the field of view decreases. For example, a compressed stored electrogram gives a detailed "telephoto" view of an arrhythmia. Two seconds of electrogram information typically will occupy a memory page consisting of 256 eight-bit words. The prior known technique of storing marker chains offers an intermediate "normal" view. A marker chain covering approximately one minute occupies a memory page.

As realized by the inventors, this limitation is particularly constraining in implantable devices for detecting tachycardias and tachyarrhythmias, such as cardioverters and defibrillators. This is because in these devices it is important first to determine power level of the therapy to be applied, and second, to determine or analyze the results of the therapy. Hence, it is desirable to have a record of activity prior to and following the delivery of the therapy. Typically, the time period extends from two seconds prior to two seconds after the delivery of the shock for cardioversion or alefibrillation. Further, to determine the effectiveness over the long term of the therapies applied by the implanted device, it is desirable to obtain information on the cardiac rhythm which occurs between patient visits to the physician, and to include information that is more analytic than a review of the histogram data such as is stored in the known implantable devices.

It is, therefore, an object of this invention to provide an improved implantable Holter function in an implantable device, notably a device for arrhythmia monitoring or therapy, wherein the improvement comprises storing information about an arrhythmia episode at several levels of detail, with increasing levels of detail corresponding to shorter recording periods. With reference to the photograph analogy, the invention provides a "zoom" feature. The zoom feature permits selecting different "focal lengths", in that each focal length selects a different degree of detail. Each focal length thus may contain the same amount of data, but at a different resolution (level of detail), such that the greater the level of resolution (detail), the shorter the real-time period that level of data represents.

It is a further object of this invention to introduce a novel implantable Holter function called an "event log," which records data/time-stamped events, but which occur less frequently than the events in the known marker chains, thus permitting coverage of a longer time period than a marker chain in the same memory space. Again referring to the photograph analogy, the Holter function event log provides a "wide angle" view of cardiac activity.

It is a further object of the invention to provide a way to display the relation in time of the recordings at different levels of detail.

It is yet a further object of this invention to provide logic for arbitrating which of the arrhythmia episodes the device saves in its memory.

Still another object of this invention is to permit an external programing device selectively to reserve sections of memory for other uses than implantable Holter functions, such as program storage (i.e., software instructions for a microprocessor, such as in the aforementioned CHORUS II devices).

Broadly, the present invention concerns a device for recording Holter function information, for use with a medical device having cardiac pacing and sensing functions, comprising: detection means for acquiring information about the state of a patient or the device and convening it to a digital representation; a clock for determining at least one time interval; an addressable memory that is partitioned into sectors for durably storing information including distinct record entries; triggering means, responsive to the detection means and the clock means, for recognizing the occurrence of at least one predetermined type of event, and for providing a triggering signal upon said recognition corresponding to said predetermined type of event; and first treatment means responsive to said triggering signal, for combining data from the detection means, the clock, and the triggering signal, to form a first record of the event at a first level of detail spanning a first period of time, and for storing said first record in a first sector in the memory. The term "treatment means" is used to refer to a digital signal processing device such as a microprocessor, microcontroller or computer executing a sequence of software instructions, or a logic circuit state machine, constructed to perform the required data input/output and manipulation.

Preferably, the device further includes a second treatment means, also responsive to the triggering signal, for combining data from the detection means, the clock, and the triggering signal, to form a second record of the same event at a second level of detail spanning a second period of time, and for storing said second record in a second sector in the memory, where said second level of detail includes less detail than said first level, and where said second period of time exceeds said first period of time.

In one embodiment, the second treatment means stores an event log comprising a plurality of event log entries, for logging events which occur less frequently than pacing and sensing events. Typically, each event log entry contains a stored code for the type of event, at least one additional stored parameter concerning the state of said patient and/or the state of the medical device, and stored information indicating the time of occurrence of the event.

One of the types of predetermined types of events is the passage of a predetermined interval of time measured by the clock, for recording event log entries at a predetermined frequency. In such case, the additional stored parameter concerning the state of the patient and/or device is the count, over the predetermined interval of time, of any one or more of the following parameters: the number of ventricular sensed beats (a "sensed" beat being a detected spontaneous cardiac depolarization), the number of atrial sensed beats, the number of sensed premature ventricular contractions (also known as extrasystoles), the shortest measured ventricular cycle length, and the average length of last predetermined number of ventricular cycles.

In one embodiment, the detection means operates to classify the cardiac rhythm into categories including, for example, sinus rhythm, and one or more classes of tachyarrhythmia. In this embodiment, one of the predetermined types of events includes a change in the cardiac rhythm classification, and the additional stored parameter (or parameters) concerning the state of the patient and/or device includes one or more of the following parameters: the class of the rhythm; and a set of classification criteria including one or more of: rate, average rate, acceleration, rate stability, and atrioventricular association.

The present invention also is applicable to record Holter function information in devices which deliver cardiac antitachycardia pacing (ATP) therapy. In such cases, the predetermined types of events also include (in addition to the aforementioned categories when cardiac pacing and sensing functions are included) the application of a sequence of ATP to said patient. In this case, the additional stored parameter (or parameters) concerning the state of the patient and/or device includes one or more of the following parameters: an identification of the ATP program and sequence, the number of sequences delivered, the last escape interval provided, the number of cycles in last delivered sequence, and the number of cycles in which ventricular sensing occurred.

The present invention also is applicable to record Holter function information in an implantable defibrillator. In this application the predetermined types of events also include the application of shock therapy to said patient. In this case, the additional stored parameter (or parameters) concerning the state of the patient and/or device includes one or more of the following parameters: the shock program number, the number of shocks delivered in the program, the shock final voltage, the shock initial voltage, the shock duration, the shock waveform (i.e., whether it is constant tilt or constant duration), and the shock charge time.

In addition, the predetermined types of events also may include one or more of the following: the occurrence of fibrillation or tachycardia requiring cardioversion or shock therapy, the occurrence of tachycardia requiring antitachycardia pacing therapy, the delivery of cardioversion or shock therapy, and the delivery of antitachycardia pacing therapy. Further, all of the aforementioned predetermined types of events that are related to cardiac pacing and sensing also may be included in such a device. It also should be understood that the above-described parameters are well-defined to persons of ordinary skill in the art familiar with antitachycardia pacing, cardioversion and defibrillation, and are used in their conventional manner.

In one application of the present invention, the treatment means, or one of the treatment means when more than one is used, stores a chain of event markers for marking pacing and sensing events. Preferably each event marker includes a first code for the type of event and a second code corresponding to the time of occurrence of each marked event. These codes are used so that an external programmer can, by telemetry, access the stored marker chains and determine the time that the marked event occurred, using the codes.

In the embodiment where two treatment means are used, the first treatment means may store an electrogram, and the second treatment means may store a marker chain. Alternatively, the first treatment means may store a marker chain, and the second treatment means may store an event log. Another alternative is that the first treatment means stores an electrogram and the second treatment means stores an event log.

In another embodiment of the present invention a third treatment means is included which operates in the same manner as the first and second treatment means, namely to form a third record of the event at a third level of detail spanning a third time interval, and for storing the third record in a third sector in the memory. Thus, in one application of this embodiment, the third level of detail may contain less details than the second level of detail and correspondingly the third time interval spans a greater period than the second time interval. In an example of such a device, the first treatment means may store an electrogram, the second treatment mean may store a marker chain, and the third treatment means stores an event log.

In accordance with another aspect of the invention, the foregoing device, in any of its embodiments is combined with, or rather is a part of, a medical device for implantation in a human patient, and includes a system for memory management for storing data representing implantable Holter functions. In this embodiment, the aforementioned implant also includes a telemetry system to permit access and retrieval of records stored in the addressable memory by an external programmer. External programmer devices are conventionally associated with implanted medical devices, for readout via telemetry and display of stored information. The telemetry system also allows the external programer to reprogram remotely the implanted device processing software and/or programmable values. The invention further includes means for selecting which of the memory sectors to use for storing information corresponding to the next episode, upon completion of storage of information corresponding to the most recent previous episode. As used herein, an episode is one or more of the same type of predetermined events. Preferably, the selecting means includes at least one of the following: means to avoid changing the presently selected sector when an external programmer selectively instructs said implantable device to avoid changing it, for permitting the external programmer to read other sectors without risk of the implant simultaneously writing to the other sectors during the telemetry readout; means to avoid selection of a sector selectively designated as reserved for a use other than storing event information, which sector is called a "reserved" sector; means to avoid selection of a sector which contains a stored event that has not yet been read by an external programmer, which sector is called an "unerased" sector; means to avoid selection of a sector which contains a stored episode of a type designated to save until it has been read out, which sector is called a "priority" sector; and means for said implantable device to select the next sector according to the age of the stored episode, to provide for writing over the oldest event records.

In such a device, the stored episodes preferably include at least one of the occurrence of fibrillation or tachycardia and the application of cardioversion or shock therapy, and the occurrence of tachycardia and application of antitachycardia pacing therapy.

Preferably, the selecting means, when so enabled by an external programmer, executes one of the following operations to arbitrate storage of episodes when the memory allocated for implantable Holter information is filled: attempts to select the next sector that is not defined as unerased or reserved; if it finds no such unreserved or unerased sector, seeks the sector containing the oldest episode which is not a designated priority sector; and if it still does not find an unreserved sector which is not designated a priority sector, selects the sector containing the last episode stored and writes over the last episode stored. It should be understood that the selecting means is preferably implemented as a sequence or a number of sequences of program instructions for controlling the operation of a microprocessor to perform various operations on the acquired data, depending on the status of various software flags and the state of the memory. Of course, it also could be implemented in solid state circuitry.

BRIEF DESCRIPTION OF THE DRAWINGS

Further features of the invention, its nature and various advantages will be more apparent from the accompanying drawings and the following detailed description of the invention, in which:

FIG. 2 shows an example of a display screen of an external programer for selecting for display implantable Holter records stored in accordance with the apparatus of FIG. 1; and FIG. 3 illustrates an example of an event log display on a programer display screen.

DETAILED DESCRIPTION OF THE INVENTION

Figure 1:
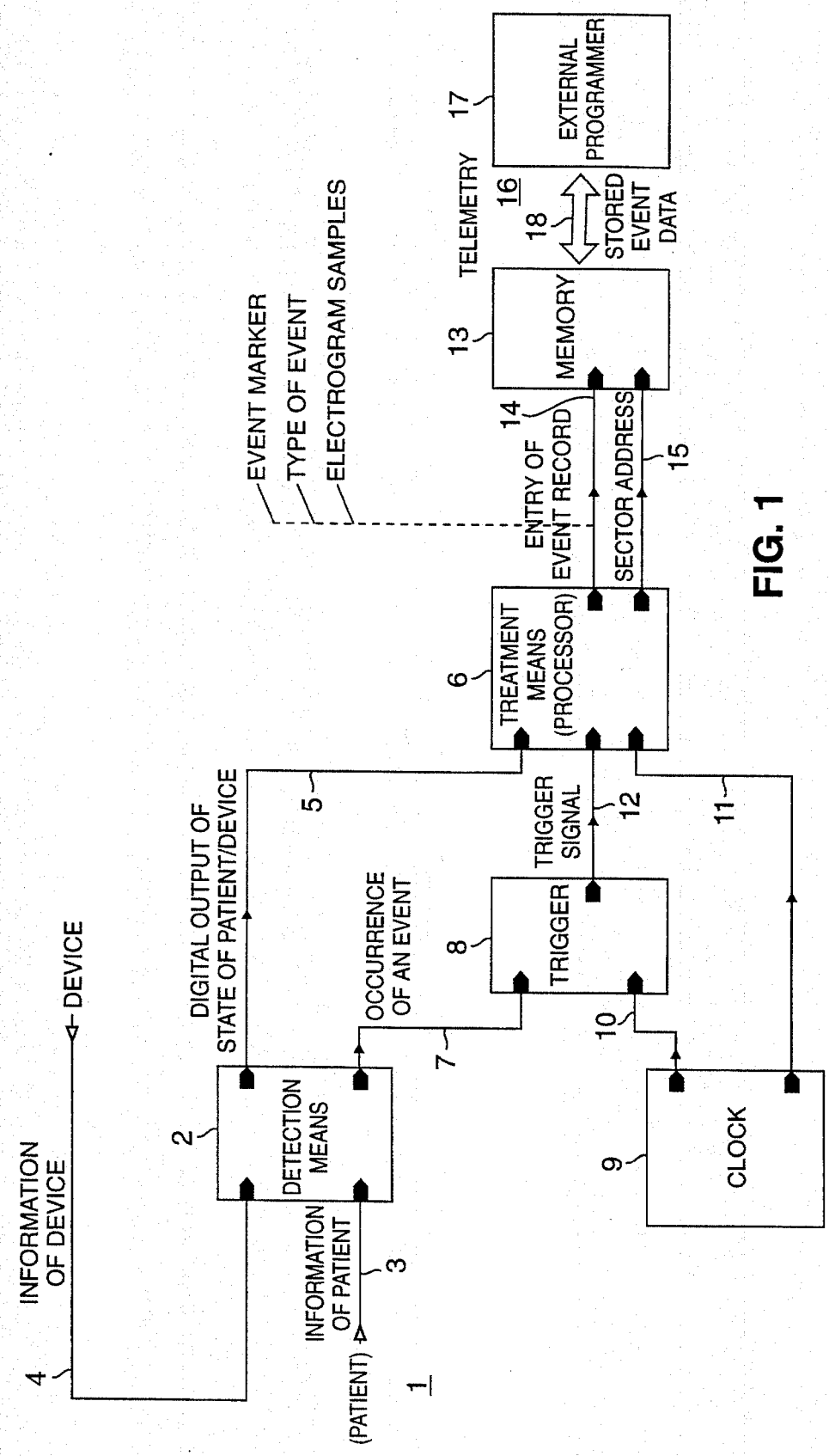
FIG. 1 shows a block schematic diagram of a preferred embodiment of the present invention and the data flow between the elements.

Referring to FIG. 1, the elements in a medical device in accordance with the present invention intended for implant in a human patient 1, and an associated external programer 17, are shown. The apparatus of the present invention includes detection means 2 for acquiring information 3 concerning the patient 1, and for acquiring information 4 concerning the operation of the device itself. The detection means 2 converts the information 3 and 4 into a digital representation 5 for treatment by treatment means 6, i.e., the digital processor. The detection means 2 also provides information 7 permitting triggering means 8 to determine the occurrence of predetermined events concerning the state of the patient or device and to discriminate these events according to their nature.

Still referring to FIG. 1, the invention also contains a clock 9, called a Holter clock, for measuring intervals between events and for timing one or more predetermined intervals. The clock 9 has an output 10 for signalling the triggering means 8 when the end of a preselected timed interval occurs. The clock 9 has a second output 11 which permits the treatment means 6 to determine the present time and with it to construct a time stamp, i.e., the date and time (functioning as a real-time or an elapsed-time clock).

Triggering means 8 issues a trigger signal 12 to the treatment means 6, when the detection means 2 signals the occurrence of a predetermined event via signal 7, or when the clock 9 signals the end of a timed interval via signal 10. The trigger signal 12 contains sufficient information to identify the type of predetermined event which occurred.

The device also contains a memory 13, called a Holter memory, which is partitioned as described below. The memory 13 receives event data 14 from the treatment means 6, and the treatment means 6 signals the memory 13 via an address 15 where (i.e., in which sector and at what location within that sector) to store the event related data.

Also shown in FIG. 1, is a telemetry link 16 permitting an external programmer 17 to interrogate stored event episode data (arrow 18) from the memory, for analysis and display of the stored event data.

The treatment means 6 combines the digital information 5 concerning the state of the patient or the device or both from detection means 2, with the identification of the type of triggering event from the trigger signal 12, and information on the present time 11 from the clock 9. These data produce the event entry 14 to be stored in the memory 13. The treatment means 6 also determines the memory address 15 wherein to store this event entry.

The invention also provides for multiple triggering means (not shown in FIG. 1) for triggering on different predetermined events, and for multiple treatment means (also not shown) for providing different types of event entries in response to one or more trigger signals. The principle of operation of these multiple triggers and/or treatment means remains the same as for the above described devices shown in FIG. 1, although different decision making criteria are used. In essence, the multiple means may be different sections of software, for operating on the same sensed input data in different ways, or different logic circuits when implemented in a hardware form.

Three examples of the types of event entries 14 encompassed by the invention are: electrogram samples, event markers, and event log entries.

An electrogram sample is a digital representation of the instantaneous voltage signal measured by electrodes placed directly on the heart. The number of samples per second can be reduced by various published compression algorithms. The device can store electrogram samples at a fixed intervals, or at varying intervals.

An event marker is a digital code indicating the type of event marked, and an accompanying digital code indicating the time of occurrence of the event. The device stores event markers for pacing and sensing events.

An event log entry is a digital code indicating the type of event entered, a digital code representing at least one additional stored parameter concerning the state of the patient and/or the state of the implantable device, and a code indicating the time of occurrence of the event. The device stores such information codes for events which occur less frequently than pacing and sensing events; for example, for the application of antiarrhythmia therapy.

To achieve simultaneous display of information about events at different levels of detail in accordance with the invention, and to indicate the relation in time between the representations at different levels of detail, the device of the present invention provides a "time-stamp" for the event entries. This means that the device must store sufficient information about event entries so that an external programmer can reconstruct a timing diagram. For this, the external programmer must know the time between any pair of event entries. The device can use for example, one of the following techniques for time-stamping, as appropriate.

First, when the device records entries at a fixed interval, such as electrogram samples obtained at constant frequency, or event log entries recorded once each minute, then it can simply time-stamp one of the events. The programmer uses the fact that the time interval between any two adjacent samples remains fixed to calculate the time of each sample.

Second, when the device records entries at a varying interval, it must time-stamp each entry. It can stamp the time passed since the previous entry, or it can stamp the value of the Holter clock at the time when it stores the entry.

Third, if the interval between events cannot exceed some predetermined value, then the device only needs to store certain digits of the clock time, only those digits with less significance than this predetermined value. For example, if entries never occur more than one minute apart, the device only needs to store the second at which each event occurred. The programmer can calculate the time between events by knowing the second at which each event occurred, and knowing that less than one minute passed between events. By these techniques, the amount of memory required for date-stamping the recorded entries is minimized.

EXAMPLES

Set forth below is an example of an application of the invention illustrated in FIG. 1 in the case when the medical device is an implantable defibrillator and three treatment means are used. This example uses the advantageous principles of the present invention to store information about cardiac arrhythmia episodes, but should be considered as illustrative and not limiting. Its application to recording implantable Holier functions in simple pacemakers and antitachycardia pacemakers as well as to external Holier recorders should be understood as within the scope of the invention.

In this example, arrhythmia detection circuits and software (collectively shown at 2 in FIG. 1) familiar to those skilled in the art detect and report the present cardiac rhythm from electrograms (shown at 3 in FIG. 1).

The device maintains a real-time Holter clock 9 (FIG. 1) for time-stamping stored events. It has a resolution of 15.6 ms, in five bytes of eight bits each. The Holter clock has the following characteristics:

| byte | resolution | range |
|------|------------|-------|
| 4 | 2.13 years | 545 years |
| 3 | 3.03 day | 2.13 years |
| 2 | 17.1 min | 3.03 day |
| 1 | 4.00 sec | 17.1 min |
| 0 | 15.6 ms | 4.00 sec |

The Holter clock 9 shown also contains two timers (common in the known pacemakers) to provide regular signals (collectively shown at 10 in FIG. 1) indicating the end of a timed interval. One timer gives a signal each 7.81 milliseconds, to indicate when to store an electrogram sample. Another timer gives a signal each minute, to indicate when to store certain event log entries.

The memory 13 is partitioned so as to store event entries in groups. The memory is thus segmented into a number of records, where each record corresponds to an episode. An episode contains a single cardiac arrhythmia. The episode includes detection of the arrhythmia, application of therapy (perhaps repeated), and evidence of successful conversion of the arrhythmia.

The device further divides each record into pages. Each page contains a single type of event entry. Each record contains five pages of 256 bytes (where each byte contains 8 bits). The five pages contain: (1) An event log for the entire arrhythmia, consisting of sequential event log entries, (2) a first electrogram taken during a 2 second period before the device first calls for therapy (a so-called "initiation ECG"), consisting of sequential electrogram samples, (3) A first marker chain saved at the end of the initiation ECG, consisting of sequential event markers, (4) A second electrogram, taken for up to 2 seconds after the device pronounces success (a so-called "conversion ECG"), and (5) A second marker chain, saved at the end of the conversion ECG.

In the treatment means, in this case processing software (shown at 6 in FIG. 1), to manage the Holter memory, the device maintains (elsewhere in memory 13, outside the stored Holter information records) an index to the current record, and a flag which the external programmer controls, to enable or disable the device from selecting a new record as the current record. In this way, the programmer can insure that the device does not write to a record while the programmer is reading it.

It also maintains the following information for each record:

Time-stamp, the Holter clock value when the device saves the record, with a precision of 4 seconds.

Reserved, indicating when asserted that the programmer has reserved the sector for storing program instructions, not Holter data.

Event, indicating whether the record is:
  erased (a code set by the programmer once it has read the record),
  ventricular tachycardia (VT), one type of arrhythmia identified by the detection means 2,
  persistent sinus tachycardia (ST) or superventricular tachycardia (SVT), other types of arrhythmias identified by detection means 2, or
  ventricular fibrillation (VF), yet another type of arrhythmia.

Having explained the partition of the Holter memory 3 into pages, an example of the internal structure of each page is described. Each page contains a chain of event entries. In this example, event logs have 8 bytes per entry, the electrograms have 1 byte per entry, and markers have 2 bytes per entry. The first byte of each event cannot contain codes FFH or FEH, which the device uses to mark chain start and end. For an event log, the device saves eight bytes for each event. The first byte codes the event type. The second byte stores one byte of the Holter clock with a resolution of 4 seconds (to determine time between events). The remaining six bytes depend on the event type and the data to be stored.

For markers, the device saves two bytes for each event: the event marker code (but never FFH nor FEH) and the time since the start of the ventricular pacing cycle, in units of 15.6 ms.

For electrograms, the device saves one byte each 7.81 ms, representing the electrogram amplitude with an amplitude range of −32 to +31 counts. Each count has a weight (i.e., is an increment) of approximately 0.30 reV.

When starting a chain, the device writes FFH to the first byte of the first event. It sets the pointer showing where to write the next event, to the second event in the page. When ending a chain, it writes FEH to the first byte of the next event.

When reading the page, if the first byte contains FFH, and if the first byte of the second event contains FEH, then the chain is empty. Otherwise, the chain starts on the second event and ends on the event before the next event marked with FEH. If the first byte does not contain FFH, the chain starts on the event after the one marked with FEH and ends on the event before it.

Having described the structure of the clock 9 and the memory 13, the following gives an example of the functioning of the detection (2), triggering (8) and treatment (6) means for storing an "episode" in memory. Techniques commonly exist for implementing these means in implantable devices, including microprocessor-based devices executing software, and very-large-scale integrated (VLSI) circuits with dedicated state machines.

With reference to FIG. 1, the sequence of operation of the triggering and treatment functions is as follows.

Step 1. When the detection means 2 (namely the circuits and/or software) signal the triggering means 8 via signal 7 that the cardiac rhythm has changed to a tachyarrhythmia, the triggering means 8 sends a trigger signal 12 to the treatment means 6, indicating the type of arrhythmia. In response, the treatment means 6 starts storing an event log and initiation markers for this new arrhythmia. It obtains event and marker data 5 from detection means 2. The detection means 2 gets some event data 3 from the patient 1, and other event data 4 from the device itself. One example of event data 4 would be initiation of antiarrhythmia therapy.

Step 2. When the detection means determines that there could be less than two seconds remaining before calling for therapy (i.e., starting antitachycardia pacing or starting to charge the shock capacitors for delivering either a cardioversion or defibrillation therapy), the triggering means 8 signals the treatment means 6 via a new trigger signal 12 to start recording the initiation ECG. The treatment means 6 obtains electrogram data 5 from detection means 2.

Step 3. If thereafter the detection means 2 finds there is more than two seconds before calling for therapy, then it informs the triggering means, which in turn informs the treatment means to return to detection; that is do not save the record in progress, but instead prepare to save this or the next arrhythmia in the same record. Otherwise, if the detection means proceeds to call for therapy, then continue as described below (in the description below, the detection means continues to provide control and data signals to the triggering and treatment means as explained above).

Step 4. Temporarily memorize the event which started the arrhythmia: VF, sustained fast rate (FR) (i.e., ST, SVT), or VT. The device will store this as the event type after successful conversion of the arrhythmia. Then recording of the initiation ECG is stopped and its end marked. The end of the initiation markers is marked and the device starts storing conversion markers. Since the device stops electrogram and markers at the same time, the programmer can align them to display them concurrently.

Step 5. After detecting a successful conversion, start counting four cycles of the conversion ECG. If during these four cycles the tachyarrhythmia detector finds a new arrhythmia, and it is less than two seconds from calling for therapy for the new arrhythmia, then proceed directly to the next step. Otherwise, proceed to the next step after the device records at least four cycles.

Step 6. After recording the conversion ECG, mark the end of the conversion ECG, the conversion markers, and the event log. Record the time stamp and the event type.

Then, select the next record. If at least 3 records are available for Holter information, the device should save the latest VF and the latest sustained fast rate (FR). To select the next record, if the programmer has enabled selecting the next record, the implant first looks for an unreserved erased record. If it does not find any, it looks for the oldest unreserved record which is not a unique VF or a unique FR. If it still does not find any, it continues to write over the last record.

If the detector says it could call for treatment of a new arrhythmia in less than two seconds, proceed immediately to recording the new initiation ECG. Otherwise start tachyarrhythmia detection, waiting for the next arrhythmia.

That concludes the discussion of the sequence of operation of the invention of this Example.

The description above explained that electrogram samples consist simply of digitized six-bit samples of electrogram voltage, possibly compressed. The description below gives examples of the types of event which the device can store as event markers and event logs.

Pacing markers: The device marks the following events in marker chains: P in refractory, P sense, A pace, R in refractory, R sense, V pace.

For the basic pacemaker event log entries, each minute the device stores the following information: a code identifying the log (80H); a count of the number of ventricular detections sensed; a count of the number of atrial detections sensed or atrial detections sensed during the refractory period; a count of premature ventricular contractions (pvc); the shortest ventricular cycle; an average of the last 4 ventricular cycles; and 0 (zero).

For arrhythmia detection event log entries; each time the detected rhythm changes, the device stores an event log entry with: a code to identify the log as a detection (40H); the type of rhythm; a PR correlation (a detection characteristic based on the interval between the P and the following R events); the RR correlation (another detection characteristic based on the interval between successive R events); the type of cardiac acceleration; the classification of the last cycle; an average of the last 4 RR (ventricular cycle lengths).

For antitachycardia pacing (ATP) event log entries, after delivering any ATP sequence, just before entering redetection, the device stores the following information: a code to identify the log as ATP (20H); the ATP program number; the number of ATP sequences delivered; the last escape interval provided; the number of cycles in the last sequence delivered; the number of cycles in which ventricular sensing occurred; and 0 (zero).

For the shock delivery event log; after delivery of each shock, the device stores the following information: the program number; the number of shocks delivered in program; (shock final voltage—14.2 V)/25 V; (stored voltage after charging—14.2 V)/25 V; the sum of shock phase durations/0.24 ms; 1 if the shock waveform was constant tilt, else 0; the shock charge time/0.25 s.

That concludes the description of the elements of the invention in the implanted device.

The device also contains a telemetry link shown at 18 in FIG. 1 to an external programmer shown at 17.

FIG. 2 shows an example of a programmer display screen for selecting a Holter record to display. The screen 19 displays the presently selected record number, e.g., No. 3, and screen 20 displays a brief description of the record. It also has "buttons" 21 and 22 enabling the user to read and display the selected record (21), or to "erase" it (22). "Erasing" frees (releases) the record for the implant to write over it, as explained previously.

The Holter display screen for a record needs to show three types of information: event log, marker chains for start and end of arrhythmia, and electrogram snapshots for start and end.

The screen header could show the record number, arrhythmia type, date, and time; for example:

Holter record 3, VF, 10 Sep 92, 11:24

The programmer can display event logs in a band at the top of the screen 23 as shown in FIG. 3. The first line in FIG. 3 shows the event time (with 4 second resolution) and event number (E1 is the first event stored in the log). Marker chains use the event number to show in which cycle the event occurred.

On the same screen it can concurrently display marker chains (at 25 mm/see) when available, in a band at the center of the screen, and electrograms (also at 25 mm/sec) when available, in a band at the bottom of the screen. It can display a time scale between the marker display and the electrogram display. When it needs to display electrogram or markers it will need a fixed horizontal time scale, and thus it must display horizontal space between event log entries.

Since there is a marker in the marker chain for each event log, the display can show in the marker chain exactly on which cycle each event log occurred. One convenient way would be to display a line over the marker chain, with each event number over the cycle to which it corresponds.

The user can move the display backward and forward in time with the left and right cursor keys. When there is no electrogram or marker showing, the cursor keys move to the next event log entry. When there is an electrogram or marker showing, the cursor keys move one second right or left.

This description assumes the presence of a telemetry system for wireless bidirectional communication of digital data between the implant and an external programming and display device. Implantable medical electronic devices have included such systems for over fifteen years, so the prior an adequately describes how to implement them and it is within the ability of a person of ordinary skill in the an to adapt such devices for use with the present invention.

Although the invention has been described with reference to a particular embodiment, it is to be understood that this embodiment is merely illustrative of the application of the principles of the invention and not limiting. Numerous other modifications may be made and other arrangements may be devised without departing from the spirit and scope of the present invention.

We claim:

1. Apparatus for recording Holter function information for a medical device including cardiac pacing and sensing functions, comprising:

detection means for acquiring information representative of the state of one of a patient and the medical device and convening it to a digital representation;

a clock having a time signal output including at least one predetermined time interval;

an addressable memory partitioned into sectors for storing distinct information entries;

triggering means, responsive to said detection means and said clock output, for recognizing the occurrence of at least one predetermined type of event, and providing a triggering signal upon said recognition corresponding to said predetermined type of event;

first treatment means responsive to said triggering signal, for combining data from said detection means, said clock output, and said triggering signal, to form a first record of said event at a first level of detail spanning a first period of time, and for storing said first record in a first sector in said memory; and second treatment means responsive to said triggering signal, for combining data from said detection means, said clock, and said triggering signal, to form a second record of said event at a second level of detail spanning a second period of time, and for storing said second record in a second sector in said memory, wherein the second level of detail includes less detail than said first level, and where said second period of time exceeds said first period of time.

2. The apparatus of claim 1 wherein the second record further comprises an event log comprising a plurality of event log entries corresponding to events which occur less frequently than pacing and sensing events, wherein each event log entry contains a stored code for the type of event, at least one additional stored parameter concerning the state of one of said patient and said medical device, and stored information indicating the time of occurrence of the event.

3. The apparatus of claim 2, wherein one of said predetermined types of events comprises a predetermined interval of time measured by said clock means, wherein the triggering means further comprises means for recording event log entries at a predetermined frequency in response to said predetermined time interval.

4. The apparatus of claim 3 wherein the additional stored parameter comprises a count over said predetermined interval of time of at least one parameter selected from among the group consisting of:

a number of ventricular sensed beats, a number of atrial sensed beats, a number of sensed premature ventricular contractions, a shortest measured ventricular cycle length, and an average length of a last predetermined number of ventricular cycles.

5. The apparatus of claim 2 wherein the medical device functions include means for sensing a cardiac rhythm, wherein said detection means further comprises means for classifying a cardiac rhythm into categories including a sinus rhythm and at least one class of tachyarrhythmia, wherein one of said predetermined types of events comprises a change in cardiac rhythm classification, and wherein the additional stored parameter comprises at least one of the rhythm class, and a set of classification criteria including one or more of: rate, average rate, acceleration, rate stability, and atrioventricular association.

6. The apparatus of claim 1 wherein the medical device functions include delivering cardiac antitachycardia pacing (ATP) therapy, wherein one of said predetermined types of events includes the application of a sequence of ATP.

7. The apparatus of claim 6 wherein the additional stored parameter is selected from among the group consisting of:

an identification of an ATP program and sequence, a number of ATP sequences delivered, a last escape interval provided, a number of cycles in the last delivered sequence, and a number of cycles in which ventricular sensing occurred.

8. The apparatus of claim 2 wherein the medical device functions include an implantable means for delivering a shock therapy for defibrillation, wherein one of said predetermined types of events includes an application of shock therapy, and wherein the additional parameter is selected from among the group consisting of:

a shock program number, a number of shocks delivered in program, a shock final voltage, a shock initial voltage, a shock duration, a shock wave form, and a shock charge time.

9. The apparatus of claim 8 wherein said predetermined types of event include one or more of the following:

an occurrence of one of a fibrillation and a tachycardia requiring cardioversion or shock therapy, an occurrence of a tachycardia requiring an antitachycardia pacing therapy, a delivery of a cardioversion or shock therapy, and a delivery of an antitachycardia pacing therapy.

10. The apparatus of claim 1 wherein each said first record further comprises a chain of event markers for marking pacing and sensing events, wherein each event marker comprises a first code corresponding to the type of event and a second code corresponding to the time of occurrence of each marked event.

11. The apparatus of claim 1 wherein each said first record further comprises an electrogram, and each said second record further comprises a marker chain.

12. The apparatus of claim 1 wherein each said first record further comprises a marker chain, and each said second record further comprises an event log.

13. The apparatus of claim 1 wherein each said first record further comprises an electrogram and each said second record further comprises stores an event log.

14. The apparatus of claim 1 further comprising a third treatment means responsive to said triggering signal for combining data from said detection means, said clock signal, and said triggering signal, to form a third record of the event at a third level of detail spanning a third time interval, and for storing said third record in a third sector in said memory means, wherein the third level of detail contains less details than the second level of detail and the third time interval spans a greater period than the second time interval and wherein said first record further comprises an electrogram, said second record further comprises a marker chain, and the third record further comprises an event log.

15. The apparatus of claim 1 wherein the medical device further comprises a medical device for implantation in a human patient and a system for memory management for an implantable Holter function, the apparatus further comprising:

a telemetry system associated with said medical device for providing access to and retrieval of said stored records in the addressable memory by an external programer, and to allow remotely reprogramming said medical device; and means for selecting which of said partitioned memory sectors to use for storing information corresponding to a following episode, upon completion of storage of information corresponding to a preceding episode, said means for selecting comprising at least one of the following:

means to avoid changing the presently selected sector when said external programmer selectively instructs said implantable medical device to avoid changing it, for permitting said external programmer to read other sectors without risk of said implant simultaneously writing to said other sectors during readout, means to avoid selection of a sector selectively designated as reserved for use other than storing event information, said sector called a "reserved" sector, means to avoid selection of a sector which contains a stored episode not yet read by said external programmer, said sector called an "unerased" sector, means to avoid selection of a sector which contains a stored episode of a type designated to save until readout, said sector called a "priority" sector, and means for said implantable device to select the next sector according to the age of the stored episode, for writing over the oldest episode.

16. The apparatus of claim 15 wherein said episodes include at least one of the following:

an occurrence of a fibrillation or a tachycardia and application of a cardioversion therapy, and an occurrence of a tachycardia and an application of an antitachycardia pacing therapy.

17. The apparatus of claim 15 wherein said selecting means, when enabled by said external programmer, executes one of the following operations:

(1) attempts to select the next unreserved sector that is not an unerased sector, (2) if it finds no unreserved sector that is not an unerased sector, seeks the oldest unreserved episode which is not a designated priority episode, and (3) if it still does not find an unreserved sector which is not designated a priority sector, selects and writes over the last episode stored.

18. A method for recording Holter function information for a medical device including cardiac pacing and sensing functions comprising:

(a) acquiring information about a patient or said device and convening it to a digital representation;

(b) providing a clock signal including at least one predetermined time interval;

(c) providing an addressable memory for durably storing information into memory sectors partitioned for storing distinct entries;

(d) recognizing the occurrence of at least one predetermined type of event in response to at least one of the acquired information and the clock signal, and providing a triggering signal upon said recognition corresponding to said predetermined type of event;

(e) responding to the triggering signal by combining data from the clock signal and the triggering signal, forming a first record of said event at a first level of detail spanning a first period of time, and storing said first record in a first sector in said memory; and (f) responding to the triggering signal by combining data from the acquired information, the clock signal, and the triggering signal forming a second record of said event at a second level of detail spanning a second period of time, and storing said second record in a second sector in said memory, wherein the second level of detail includes less detail than said first level, and wherein the second period of time exceeds said first period of time.

19. The method of claim 18 wherein forming the second record further comprises forming an event log comprising a plurality of event log entries, logging events which occur less frequently than pacing and sensing events, and providing each event log entry with a stored code for the type of event, at least one additional stored parameter concerning at least one of the state of said patient and the state of the medical device, and stored information indicating the time of occurrence of the event.

20. The method of claim 19, wherein step (d) further comprises recognizing the passage of the predetermined time interval measured as one of said predetermined types of events for recording event log entries at a predetermined frequency.

21. The method of claim 20 wherein providing the additional stored parameter comprises determining the count over said predetermined interval of time of at least one parameter selected from among the group consisting of:

a number of ventricular sensed beats, a number of atrial sensed beats, a number of sensed premature ventricular contractions, a shortest measured ventricular cycle length, and an average length of a last predetermined number of ventricular cycles.

22. The method of claim 19 wherein step (a) further comprises sensing a cardiac rhythm and classifying the cardiac rhythm into categories including a sinus rhythm and at least one class of tachyarrhythmia, wherein step (d) further comprises recognizing a change in cardiac rhythm classification as one of said predetermined types of events, and wherein providing the additional stored parameter further comprises determining at least one parameter selected from among the group consisting of:

a rhythm class, and a set of classification criteria including one or more of: rate, average rate, acceleration, rate stability, and atrio-ventricular association.

23. The method of claim 18 wherein the medical device includes the function of delivering a cardiac antitachycardia pacing (ATP) therapy, wherein step (d) further comprises providing an application of a sequence of ATP as one of the predetermined types of events.

24. The method of claim 23 wherein providing the additional stored parameter further comprises determining at least one parameter selected from among the group consisting of:

an identification of the ATP program and sequence, a number of sequences delivered, a last escape interval provided, a number of cycles in last delivered sequence, and a number of cycles in which ventricular sensing occurred.

25. The method of claim 18 wherein the medical device functions include the delivery of a shock therapy, wherein step (d) further comprises recognizing an application of shock therapy as one of the predetermined types of events, and wherein providing the additional stored parameter further comprises determining at least one parameter selected from among the group consisting of:

a shock program number, a number of shocks delivered in program, a shock final voltage, a shock initial voltage, a shock duration, a shock wave form, and a shock charge time.

26. The method of claim 25 wherein step (d) further comprises recognizing one of:

an occurrence of a fibrillation or a tachycardia requiring cardioversion or shock therapy, an occurrence of a tachycardia requiring an antitachycardia pacing therapy, a delivery of a cardioversion or shock therapy, and a delivery of an antitachycardia pacing therapy.

27. The method of claim 18 wherein step (e) further comprises forming a plurality of first records for storing a chain of event markers for marking pacing and sensing events, wherein each event marker has a first code for the type of event and a second code corresponding to the time of occurrence of each marked event.

28. The method of claim 18 wherein step (e) further comprises forming a first record that is an electrogram, and said step (f) further comprises forming a second record that is a marker chain.

29. The method of claim 18 wherein step (e) further comprises forming a first record that is a marker chain, and step (f) further comprises forming a second record that is an event log.

30. The method of claim 18 wherein step (e) further comprises forming a first record that is an electrogram and step (f) further comprises forming a second record that is an event log.

31. The method of claim 18 further comprising:
   (g) responding to the triggering signal by combining data from the acquired information, the clock signal, and the triggering signal, and forming a third record of the event at a third level of detail spanning a third time interval, and storing said third record in a third sector in the memory, wherein the third level of detail contains less details than the second level of detail and the third time interval spans a greater period than the second time interval, and wherein step (e) further comprises storing an electrogram, step (f) further comprises storing a marker chain, and step (g) further comprises storing an event log.

32. The method of claim 18 wherein the medical device is for implantation in a human patient and includes a telemetry system for accessing and transmitting stored data to an external programmer and for reprogramming the medical device under control of the external programmer, the method further comprising:
   (g) storing a first record and a second record corresponding to a first arrhythmia episode in first and second sectors of the memory, and
   (h) managing the memory for storing a plurality of arrhythmia episodes comprising:
      selecting which of said memory sectors to use for storing information corresponding to a subsequent arrhythmia episode, in response to completing of storage of said first arrhythmia episode:
      avoiding to change the presently selected sector when said external programmer selectively instructs said implantable device to avoid changing it, thereby permitting said external programer to read other sectors without risk of said implantable device simultaneously writing to said other sectors during readout,
      avoiding the selection of a sector selectively designated as reserved for use other than storing event information, said sector called a reserved sector,
      avoiding the selection of a sector which contains a stored arrhythmia episode not yet read by said external programmer, said sector called an unerased sector,
      avoiding the selection of a sector which contains a stored arrhythmia episode of a type designated to be saved until readout, said sector called a priority sector, and
      selecting the next sector according to the age of the stored arrhythmia episode, for writing over the oldest arrhythmia episode stored.

33. The method of claim 32 wherein step (g) further comprises storing first and second records corresponding to one of:
   an occurrence of a fibrillation or a tachycardia and an application of a cardioversion therapy, and
   an occurrence of a tachycardia and an application of an antitachycardia pacing therapy.

34. The method of claim 32 the selecting step (h) is enabled by said external programmer, for executing one of the following operations:
   attempting to select the next unreserved sector that is not designated an unerased sector,
   if it finds no unreserved sector that is not designated an unerased sector, seeking the oldest unreserved arrhythmia episode which is not a priority arrhythmia episode, and
   if it still does not find an unreserved sector which is not designated a priority sector selecting and writing over the last episode stored.

* * * * *

UNITED STATES PATENT AND TRADEMARK OFFICE
CERTIFICATE OF CORRECTION

PATENT NO. : 5,513,645
DATED : May 7, 1996
INVENTOR(S) : Peter Jacobson and Daniel Kroiss It is certified that error appears in the above-indentified patent and that said Letters Patent is hereby corrected as shown below:

Column 1, line 27, delete "tachyarrhythmia" and insert -- tachyarrhythmia --;

Column 1, line 55, delete "Ripan" and insert -- Ripart--;

Column 1, line 60, delete "arrhythmia" and insert -- arrhythmia --;

Column 2, line 32, delete "arrhythmia" and insert -- arrhythmia --;

Column 2, line 34, delete "alefibrillation" and insert -- arrhythmia --;

Column 2, line 39, delete "arrththmia" and insert -- defibrillation --;

Column 2, line 63, delete "alefibrillation" and insert -- defibrillation --;

Column 3, line 7, delete "arrhythmia" and insert -- arrhythmia --;

Column 3, line 29, delete "arrhythmia" and insert -- arrhythmia --;

Column 7, line 64, delete "antiarrhythrnia" and insert —antiarrhythmia—;

Column 8, line 40, delete "Holier" and insert -- Holter --;

Column 8, line 41, delete "Holier" and insert -- Holter --;

UNITED STATES PATENT AND TRADEMARK OFFICE
CERTIFICATE OF CORRECTION

PATENT NO. : 5,513,645

DATED : May 7, 1996

INVENTOR(S) : Peter Jacobson and Daniel Kroiss

It is certified that error appears in the above-indentified patent and that said Letters Patent is hereby corrected as shown below:

Column 8, line 44, delete "arrhythrnia" and insert -- arrhythmia --;

Column 9, line 4, delete "arrhythrnia" and insert -- arrhythmia --;

Column 9, line 5, delete "arrhythrnia" and insert -- arrhythmia --;

Column 9, line 32, delete "Holier" and insert -- Holter --;

Column 9, line 41, delete "arrhythrnia" and insert -- arrhythmia --;

Column 9, line 46, delete "arrhythrnia" and insert -- arrhythmia --;

Column 9, line 67, delete "reV" and insert -- mV --;

Column 10, line 25, delete "tachyarrhythrnia" and insert -- tachyarrhythmia --;

Column 10, line 29, delete "arrhythrnia" and insert -- arrhythmia --;

Column 10, line 47, delete "arrhythrnia" and insert -- arrhythmia --;

Column 10, line 53, delete "arrhythrnia" and insert -- arrhythmia --;

Column 10, line 55, delete "arrhythrnia" and insert -- arrhythmia --;

UNITED STATES PATENT AND TRADEMARK OFFICE
CERTIFICATE OF CORRECTION

PATENT NO. : 5,513,645
DATED : May 7, 1996
INVENTOR(S) : Peter Jacobson and Daniel Kroiss It is certified that error appears in the above-indentified patent and that said Letters Patent is hereby corrected as shown below:

Column 10, line 63, delete "tachyarrhythrnia" and insert -- tachyarrhythmia --;

Column 10, line 64, delete "arrhythrnia" and insert -- arrhythmia --;

Column 10, line 65, delete "arrhythrnia" and insert -- arrhythmia --;

Column 11, line 14, delete "arrhythrnia" and insert -- arrhythmia --;

Column 11, line 16, delete "tachyarrhythrnia" and insert -- tachyarrhythmia --;

Column 11, line 35, delete "arrhythrnia" and insert -- arrhythmia --;

Column 12, line 6, delete "arrhythrnia" and insert -- arrhythmia --;

Column 12, line 8, delete "arrhythrnia" and insert -- arrhythmia --;

Column 12, line 19, delete "see" and insert -- sec --;

Column 12, line 40, delete "an" and insert -- art --;

Column 12, line 42, delete "an" and insert -- art --;

Column 12, line 57, delete "convening" and insert -- converting --;

UNITED STATES PATENT AND TRADEMARK OFFICE
CERTIFICATE OF CORRECTION

PATENT NO. : 5,513,645
DATED : May 7, 1996
INVENTOR(S) : Peter Jacobson and Daniel Kroiss It is certified that error appears in the above-indentified patent and that said Letters Patent is hereby corrected as shown below:

Column 15, line 29, delete "Holier" and insert -- Holter --;

Column 16, line 19, delete "tachyarrhythrnia" and insert -- tachyarrhythmia --;

Column 17, line 40, delete "arrhythrnia" and insert -- arrhythmia --;

Column 17, line 43, delete "arrhythrnia" and insert -- arrhythmia --;

Column 17, line 46, delete "arrhythrnia" and insert -- arrhythmia --;

Column 18, line 12, delete "arrhythrnia" and insert -- arrhythmia --;

Column 18, line 17, delete "arrhythrnia" and insert -- arrhythmia --;

UNITED STATES PATENT AND TRADEMARK OFFICE
CERTIFICATE OF CORRECTION

PATENT NO. : 5,513,645
DATED : May 7, 1996
INVENTOR(S) : Peter Jacobson and Daniel Kroiss It is certified that error appears in the above-indentified patent and that said Letters Patent is hereby corrected as shown below:

Column 18, line 22, delete "arrhythrnia" and insert -- arrhythmia --;

Column 18, line 23, delete "arrhythrnia" and insert -- arrhythmia --;

Column 18, line 40, delete "arrhythrnia" and insert -- arrhythmia --;

Abstract, line 2, delete "arrhythrnia" and insert -- arrhythmia --;

Signed and Sealed this

Eighteenth Day of November 1997

Attest:

BRUCE LEHMAN

Attesting Officer

Commissioner of Patents and Trademarks